United States Patent [19]

Ockuly et al.

[11] Patent Number: 5,395,328
[45] Date of Patent: Mar. 7, 1995

[54] STEERABLE CATHETER TIP HAVING AN X-SHAPED LUMEN

[75] Inventors: John D. Ockuly; Michael C. Bednarek, both of Minnetonka, Minn.

[73] Assignee: Daig Corporation, Minnetonka, Minn.

[21] Appl. No.: 183,653

[22] Filed: Jan. 19, 1994

[51] Int. Cl.⁶ .............................................. A61M 37/00
[52] U.S. Cl. .................................... 604/95; 604/280; 128/772
[58] Field of Search ..................... 604/95, 280; 128/4, 128/772, 656–658

[56] References Cited

U.S. PATENT DOCUMENTS

| | | |
|---|---|---|
| 3,374,066 | 3/1968 | Farrant .................................. 604/113 |
| 4,586,923 | 5/1986 | Gould et al. . |
| 4,920,980 | 5/1990 | Jackowski ........................... 128/786 |
| 4,960,134 | 10/1990 | Webster . |
| 4,998,182 | 3/1991 | Krauter et al. ...................... 361/394 |
| 5,025,778 | 6/1991 | Silverstein et al. ................. 128/4 |
| 5,125,896 | 6/1992 | Hojeibane . |
| 5,156,590 | 10/1992 | Vilmar ................................. 128/4 |
| 5,190,050 | 3/1993 | Nitzche .............................. 128/772 |
| 5,195,968 | 3/1993 | Lundquist et al. . |
| 5,254,088 | 10/1993 | Lundquist et al. ................... 604/95 |

Primary Examiner—Corrine Maglione
Attorney, Agent, or Firm—Scott R. Cox

[57] ABSTRACT

A steerable catheter comprised of two parts: a catheter body proximally secured to a steerable catheter handle and a catheter tip containing an X-shaped in cross-section lumen secured to the distal end of the catheter body, a pull wire passing through the catheter body and one of the arms of the X-shaped lumen of the catheter tip, one or more electrode wires passing through the catheter body and through a second arm of the X-shaped lumen of the catheter tip and a supporting flat wire passing through the two remaining opposite arms of the X-shaped lumen of the catheter tip.

14 Claims, 3 Drawing Sheets

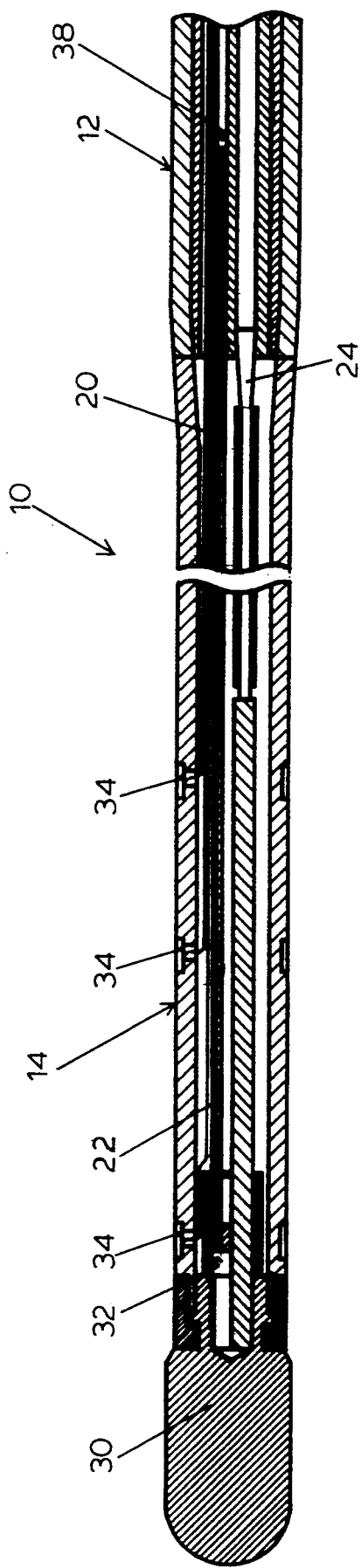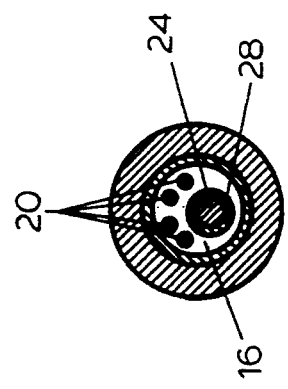

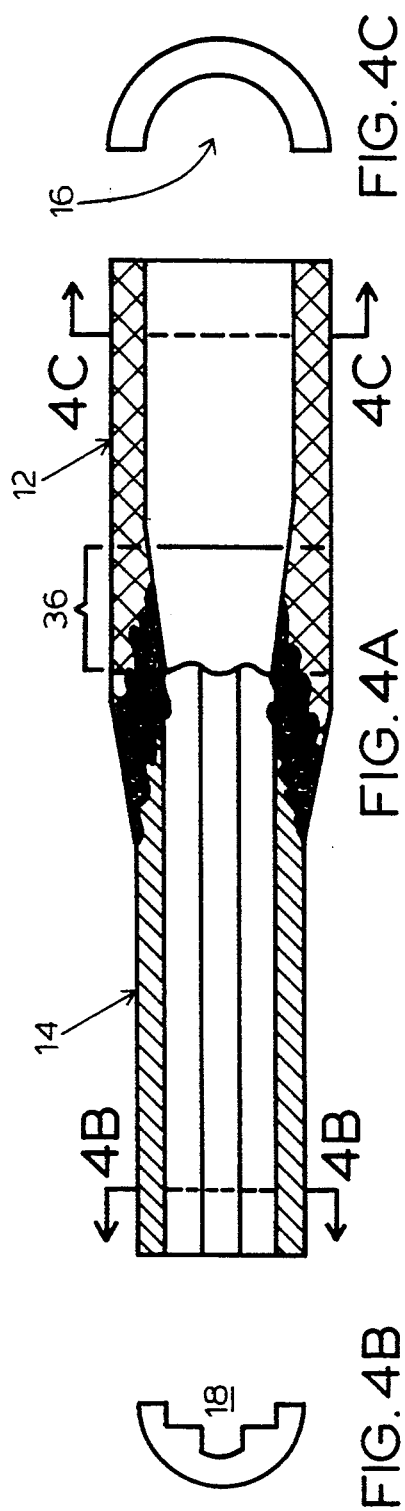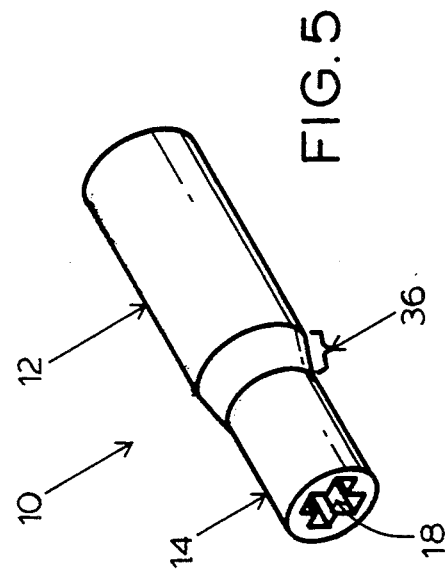

STEERABLE CATHETER TIP HAVING AN X-SHAPED LUMEN

BACKGROUND OF INVENTION

1. Field of Invention

This invention relates to steerable catheters. More particularly, this invention relates to an improved catheter tip for a steerable catheter which when bent consistently deflects within a single plane without undesired twisting.

2. Prior Art

Catheters of various types have been utilized for medical procedures for many years. For example, they have been used to convey an electric stimulus to a selected location within the human body or to monitor or make measurements for diagnostic purposes of activities within the human body. Such catheters examine, diagnose and treat areas which are otherwise inaccessible without invasive procedures. In use, the catheter is first inserted into a major vein or artery or other body lumen which is near the body surface. The catheter is then guided to the area for examination, diagnosis or treatment by manipulating the catheter through the body lumen. As the utilization of catheters in remote and difficult to reach locations within the body has increased, it has become more important to control precisely the movement of the tip of the catheter within the body lumen.

Control of the movement of catheters is difficult because of their construction. The body of conventional catheters is long and tubular. To provide sufficient control over the movement of the catheter, it is necessary that these tubular catheters be made somewhat rigid. However, these catheters must also be flexible enough to navigate through the body lumen to arrive at the desired location within the body where the desired medical procedures will occur without harming the body lumen.

One of the early methods used to control the movement of catheters within a body lumen was by preshaping catheter tips. This construction had advantages for certain limited medical procedures, but because the configuration of the bend could not be changed after insertion and because of the difficulty in orienting the bend in the desired direction as a result of the torsional flexibility of the catheter, new improved catheters were necessary.

Short and rigid controllable tip devices have also been used for special procedures where the degree of bending of the tip could be controlled from the handle. However, these devices are not satisfactory for vascular purposes where the catheter must be long, slender and flexible throughout its entire length.

To increase the ability to move and navigate within a body, longer, flexible catheters containing steerable, deflectable tips have been designed. Because the deflectable tips of these flexible catheters are readily bendable, they can be used for a number of medical procedures which require precise control over the orientation of the catheter tip. With these devices the bending of the steerable tip is achieved by increasing or decreasing the axial compressive force on one side of the steerable tip by applying tension to a pull wire which runs the entire length of the catheter. By increasing the compressive force to one side of the tip, it is bent.

To control precisely the movement of these steerable catheters, control handles have been attached at the proximal end of the catheter body. For example, U.S. Pat. No. 4,586,923 describes certain devices useful for controlling the movement of steerable catheters. See also U.S. Pat. Nos. 5,254,088, 5,195,968, 5,186,004, 5,125,896, 5,190,050 and 4,960,134.

While use of a pull wire to deflect the tip of a steerable catheter is effective in bending the tip, the lateral movement of the catheter tips of existing devices as they are being bent is not always consistent. Further, axial rotation of the catheter tip of existing devices during the bending of the catheter tip frequently occurs resulting in imprecise and inexact location of the catheter tip. Thus, improved catheters are necessary to control the direction of bending of the tip of the catheter and restrict its axial rotation as it is being bent by the pull wire. One method to limit the lateral movement of the tip portion of the catheter while it is being bent by a pull wire is by the introduction into the catheter tip of a generally flat supporting wire. See, for example, U.S. Pat. No. 5,190,050 which discloses the use of three flat planer shims juxtaposed in sandwiched relation and mounted within the tip and body of a catheter. The use of a single flat supporting wire is also disclosed in U.S. Pat. No. 5,125,896. See also U.S. Pat. No. 4,920,980.

While this use of a flat supporting wire, either singly or in combination, does assist in maintaining the catheter tip in a single plane while it is being bent, problems relating to the torquing or twisting of the catheter tip as it is being bent still occur. Thus, new designs for catheter tips are important to provide enhanced lateral stiffness to the catheter tip during the bending process while still retaining the relatively soft feel of the tip of existing catheter.

Accordingly, it is an object of this invention to disclose an improved steerable catheter tip.

Another object of this invention is to disclose a steerable catheter tip with improved structure that permits deflection of the catheter tip only in a single plane.

Another object of this invention is to disclose a steerable catheter tip where the structure of the lumen of the catheter tip is designed to receive a supporting flat wire which will also provide additional lateral stiffness to the catheter tip.

It is a still further object of this invention to disclose an improved steerable catheter tip whose structure will permit limited axial rotation of the catheter tip while it is being bent.

These and other objects are obtained by the design of the steerable catheter of the instant invention.

SUMMARY OF INVENTION

The instant invention discloses a steerable catheter comprised of a catheter body and a catheter tip wherein the catheter tip has a single X-shaped lumen which contains preferably a single pull wire, a single supporting flat wire and one or more electrical electrode wires all located within that lumen. Preferably, the pull wire is located in one arm of the X-shaped lumen, the electrical electrode wires are located in an arm of the lumen opposite the pull wire and the supporting flat wire runs between the two remaining arms, thus effectively separating the pull wire from the electrical electrode wires. In contrast, the body of the catheter proximal to the catheter tip has a generally circular cross-sectioned lumen to contain both the pull wire and the electrical electrode wires but generally only the proximal end of the supporting flat wire. By this design, the catheter tip when bent by the pull wire will only bend in a predetermined plane and will not torque or twist during that bending process.

BRIEF DESCRIPTION OF THE DRAWINGS

FIG. 1 is a side cut away view which shows both the catheter tip and the distal end of the catheter body onto which the catheter tip is attached.

FIG. 2 is an sectioned view of the catheter tip.

FIG. 3 is an sectioned view of the catheter body.

FIG. 4A is a side cut away view of the catheter tip and catheter body showing the transition zone from the catheter body to the catheter tip.

FIG. 4B is an end view of FIG. 4A directed distally from the catheter tip.

FIG. 4C is an end view of FIG. 4A directed proximally into the catheter body.

FIG. 5 is a perspective view of catheter tip and catheter body showing the transition zone.

DETAILED DESCRIPTION OF THE PREFERRED EMBODIMENT

Figure 6:
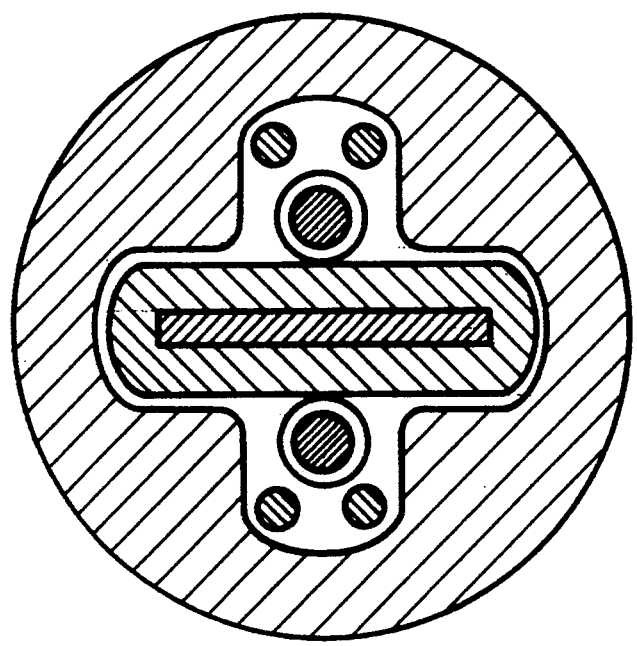
FIG. 6 is a sectioned view of the catheter top showing the use of two pull wires.

The steerable catheter (10) of the instant invention is comprised of two parts: an elongated catheter body (12) having its proximal end secured to a steerable catheter handle (not shown) and a catheter tip (14) secured to the distal end of the catheter body. The catheter body (12) is of elongated tubular construction having one or more lumen. Preferably, the catheter body has a single generally circular lumen (16). The catheter body is flexible, i.e., bendable, but substantially non-compressible along its length. The catheter body may be constructed of conventional material, such as conventional polymers. In addition, soft or pliable polymeric materials may be used for the catheter's construction such as soft thermal plastic polyolefins such as polyethylene or polypropylene, polyurethanes, polyesters or other suitable thermoplastic polymers. In the presently preferred construction, the catheter body is produced from a conventional polymer tubing with a generally soft polymer coating. Frequently it is preferred to provide a stiffening material, such as a wire braid, as part of the catheter body. The wire braid is preferably formed between an inner and outer section of the wall of the catheter body. The wire braid can be formed from a number of different, but conventional, types of material and by use of a number of conventional weaving processes. For example, the braided material may combine helical braided members with longitudinal braided members to form a reinforcing mesh. The tightness of the mesh is not critical but can be determined by the needs of the manufacturer. The braided material should have a high modulus of elasticity. The preferred braided material may be made from a metal, such as stainless steel wire, or from an aramid-type thread or other such polymer materials. The braided mesh is made by a conventional braiding process such as by braiding the material around the inner wall of the catheter with an outer wall then applied over the braided material.

The inner and outer diameters of the catheter body as well as the amount of wire braid will depend on the particular application. Notwithstanding, the lumen of the catheter body must be sufficiently large to accommodate the electrical electrode wire or wires as well as a pull wire. Generally, the catheter body is preferably circular in cross-section and is formed by a conventional extrusion process well known in the industry.

The catheter tip is generally formed separate from the catheter body. The catheter tip may be smaller in diameter than is the diameter of the catheter body. See FIG. 5. For example, if the catheter body is a 7 French the catheter tip may be a 6 French. However, the catheter tip may also be the same size or even larger in diameter than the catheter body.

The construction and shape of the catheter tip are critical to the invention. The catheter tip (18) has a single lumen shaped in the form of a "X". See FIGS. 1, 2, 4B and 5. The X-shape cross-section of the lumen of the catheter tip is formed by a conventional extrusion process.

Running inside of the X-shaped lumen are the electrical electrode wires (20), preferably a single flat supporting wire (22) and preferably a single pull wire (24). See FIGS. 1, 2 and 3. The flat supporting wire (22) is designed to fit securely into two of the opposite arms of the X-shaped lumen. See FIG. 2. On one side of the flat supporting wire in one of the remaining arms of the X-shaped lumen is placed the electrical electrode wires (20) and in the opposite arm is placed the pull wire (24). Both the flat supporting wire (22) and the pull wire (24) are preferably surrounded by a sheath (26, 28), preferably a fluoro-type polymer sheath or the like for lubricity to keep the pull wire and the flat supporting wire generally co-axial within the catheter body. The pull wire, preferably comprised of metal, extends from the steerable catheter handle to the end of the catheter tip. It is secured to the distal end of the catheter tip by conventional securing means such as by crimping or welding it in place against a tip electrode (30) at the distal tip of the catheter tip.

Alternatively, two pull wires may be used with the flat supporting wire, see FIG. 6. The purpose of the second pull wire is to permit bending of the catheter tip in the direction opposite from that of the first pull wire but in the same plane. By utilization of a second pull wire, a full 360° of rotation of the catheter tip is possible without rotation of the catheter handle or body. Where two pull wires are utilized, one is placed in one arm of the X-shaped lumen and the second pull wire is placed in the arm opposite the arm which contains the first pull wire. Preferably, see FIG. 6 the electrical electrode wires are split into two groups, with approximately half of these wires being placed within the arm of the X-shaped lumen containing the first pull wire and the remaining electrical electrode wires being placed within the arm of the X-shaped lumen containing the second pull wire. To prevent undesired contact between the pull wire and the electrical electrode wires, preferably, the electrical electrode wires which are contained within each of the arms of the X-shaped lumen will be surrounded by sheathing of the same type as is used to sheath the pull wire and the supporting flat wire. The distal end of each pull wire is preferably secured to the sheathing surrounding the flat supporting wire at or near the distal end of the flat supporting wire. Preferably the electrical electrode wire will be placed in the outer portion of the arm of the X-shaped lumen with the pull wire placed toward the center of the lumen. When the catheter tip is bent using two pull wires, the mechanism contained in the catheter and the handle for the catheter must be designed to eliminate the tension on one pull wire while increasing the tension on the opposite pull wire.

The thickness of the arms of the X-shaped lumen should be approximately the same as the thickness of the flat supporting wire (22) with its surrounding sheath so that it will not move axially or laterally within the lumen of the catheter tip. See FIG. 2. The distal tip (32) of the flat supporting wire extends to near the tip electrode (30) as is shown in FIG. 1. It is held securely in place at the distal end of the catheter tip by conventional means such as by soldering the distal tip of the flat wire in place to the pull wire.

Each of the electrical electrode wires (20) remains within one of the arms of the X-shaped lumen across from the arm containing the pull wire until the tip of each electrical electrode wire is joined with a ring electrode (34). See FIGS. 1 and 2. The distal end of each electrode wire is secured to a ring electrode (34) by conventional means such as by welding it in place. The proximal end of the electrical electrode wires is secured conventionally to electrode connectors in the handle of the steerable catheter and ultimately to the electrical monitoring, diagnosis, or treatment equipment.

The structure of the lumen of the catheter inside the distal end of the catheter body changes at or around a transition zone (36) where the catheter tip is joined to the catheter body. See FIGS. 4A and 5. The catheter tip is integrated into the catheter body by conventional means such as forcing the catheter tip into the distal end of the catheter body under heating. As the two ends are joined together and heated, the wall of the distal tip of the catheter body merges and melts into the wall of the proximal end of the catheter tip to form the transition zone. See FIG. 4A. The shape of the lumen of the catheter body gradually will change from a circular cross-section (FIG. 4C) to the X-shaped cross-section (FIG. 4B) in the catheter tip as previously discussed. See FIG. 4A. The proximal end (38) of the flat supporting wire may extend to and through the transition zone (36) between the catheter tip and the catheter body. The length of the catheter tip may vary by medical procedure. Preferably, however, the length should be at least about 2.0 inches so that the supporting flat wire will have sufficient length to prevent the axial rotation and lateral movement of the catheter tip as it is being bent. The thickness of the flat supporting wire should be at least about 0.002 inches and preferably about 0.002 to 0.004 inches to provide adequate lateral support and to prevent axial rotation during bending. The thickness of the flat supporting wire is dependent on the type of material being used and the degree of stiffness being sought. For example, flat supporting wires comprised of metal may be stiffer than flat supporting wires formed from plastic. Thus, less thickness may be required depending on the composition of the flat supporting wire.

In operation, a catheter tip (14) with an X-shaped cross-sectioned lumen (18) is formed by conventional procedures. The catheter tip with an X-shaped cross-section is secured to a conventional catheter body, preferably with a circular cross-sectioned lumen (16) also by conventional methods. Placed within the lumen of this X-shaped cross-sectioned lumen (18) is a flat supporting wire (22) with conventional sheathing (26) surrounding said wire located in two of the opposite arms of the lumen. In one of the remaining arms is placed the pull wire (24) also preferably sheathed (28) and in the other arm opposite the pull wire is placed one or more electrical electrode wires (20). The distal tip of the pull wire is secured conventionally, for example, to a tip electrode (30) located at the distal end of the catheter tip (14). The distal tip (32) of the flat supporting wire (22) is also secured in place conventionally, for example, by securing it to the pull wire near the distal end of the pull wire.

As the catheter is placed within a lumen of the human body, it may be rotated and moved to a particular location by the actions of a steerable handle secured to the proximal end of the of the steerable catheter body. The catheter tip (14) is bent from the action of placing and removing tension on the pull wire. Because of the supporting flat wire (22), the catheter tip will bend only in a single plane. In addition, because of the location of the flat supporting wire (22) within opposite arms of the X-shaped lumen of the catheter tip, additional lateral support is provided to the catheter tip during bending and, in addition, axial rotation of the catheter tip is significantly reduced. Thus, the tip of the steerable catheter can be bent precisely, regardless of the rotation of the handle of the steerable catheter.

We claim:
1. A steerable catheter comprised of
   (a) a catheter body having proximal and distal ends wherein the catheter body contains a catheter body lumen running from its proximal to its distal end,
   (b) a catheter tip secured at the distal end of the catheter body containing a lumen, wherein the lumen of the catheter tip is formed into an X-shaped cross-section forming four distinct arms within the X-shaped cross-section of the lumen,
   (c) a pull wire passing through the lumen of the catheter body and through a portion of the X-shaped lumen of the catheter tip,
   (d) one or more electrode wires passing through the lumen of the catheter body and through a portion of the X-shaped lumen of the catheter tip, and
   (e) a supporting flat wire with proximal and distal tips passing through a portion of the X-shaped lumen of the catheter tip.

2. The steerable catheter of claim 1 wherein the distal tip of the flat wire is secured to the pull wire.

3. The steerable catheter of claim 1 wherein the supporting flat wire is surrounded by a sheathing wherein the cross section of the flat wire with sheathing is longer than it is wide.

4. The steerable catheter of claim 3 wherein the width of the cross section of the supporting flat wire with sheathing is approximately the same as the width of that portion of the X-shaped lumen corresponding to the arms of the X-shaped lumen of the catheter tip containing the supporting flat wire.

5. The steerable catheter of claim 1 wherein the pull wire is surrounded by sheathing.

6. A steerable catheter comprised of
   (a) a catheter body having proximal and distal ends wherein the catheter body contains a catheter body lumen running from its proximal to its distal end,
   (b) a catheter tip secured to the distal end of the catheter body containing a single, X-shaped cross-sectioned lumen forming four distinct arms within the X-shaped cross-section of the lumen,
   (c) a pull wire passing through the lumen of the catheter body and through a portion of one arm of the X-shaped lumen of the catheter tip,
   (d) one or more electrical electrode wires passing through the lumen of the catheter body and through a portion of a second arm of the X-shaped lumen of the catheter tip opposite the arm containing the pull wire, and (e) a supporting flat wire with proximal and distal tips passing through a portion of the lumen of the catheter tip running within the two remaining opposite arms of the X-shaped lumen between the pull wire and the electrical electrode wire thus separating the pull wire from the electrical electrode wire.

7. The steerable catheter of claim 6 wherein the distal tip of the flat wire is secured to the pull wire.

8. The steerable catheter of claim 6 wherein the supporting flat wire is surrounded by a sheathing wherein the cross section of the flat wire with sheathing is longer than it is wide.

9. The steerable catheter of claim 8 wherein the width of the cross section of the supporting flat wire with sheathing is approximately the same as the width of that portion of the X-shaped lumen corresponding to the arms of the X-shaped lumen of the catheter tip containing the flat wire.

10. The steerable catheter of claim 6 wherein the pull wire is surrounded by sheathing.

11. A steerable catheter comprised of
(a) a catheter body having proximal and distal ends wherein the catheter body contains a catheter body lumen running from its proximal end to its distal end,
(b) a catheter tip secured at the distal end of the catheter body containing a single, X-shaped cross-sectioned lumen forming four distinct arms within the X-shaped cross-section of the lumen,
(c) a pair of pull wires passing through the lumen of the catheter body and through a portion of separate arms of the X-shaped lumen of the catheter tip, wherein the arms containing the pull wires are opposite each other,
(d) one or more electrical electrode wires passing through the lumen of the catheter body and through a portion of the arms of the X-shaped lumen of the catheter tip containing the pull wire, and
(e) a flat supporting wire passing through a portion of the lumen of the catheter tip running within the two remaining opposite arms of the X-shaped lumen.

12. The steerable catheter of claim 11 wherein the supporting flat wire is surrounded by a sheathing wherein the cross section of the flat wire with sheathing is longer than it is wide.

13. The steerable catheter of claim 12 wherein the width of the cross section of the supporting flat wire with sheathing is approximately the same as the width of that portion of the X-shaped lumen corresponding to the arms of the X-shaped lumen of the catheter tip containing the supporting flat wire.

14. The steerable catheter of claim 11 wherein one or more of the electrical electrode wires are surrounded by sheathing.

* * * * *